United States Patent [19]
Schweiger

[11] Patent Number: 5,789,445
[45] Date of Patent: Aug. 4, 1998

[54] METHOD FOR TOPICAL TREATMENT OF SCAR TISSUE AND RELATED TISSUE REACTION TO TRAUMA

[76] Inventor: Raymond H. Schweiger, 363 S. Bonsal St., Baltimore, Md. 21224

[21] Appl. No.: 835,422

[22] Filed: Apr. 9, 1997

Related U.S. Application Data

[63] Continuation of Ser. No. 394,000, Feb. 24, 1995.

[51] Int. Cl.⁶ .................. A61K 31/19; A61K 31/075
[52] U.S. Cl. .................. 514/568; 514/714; 514/859; 514/861; 514/863; 514/864
[58] Field of Search .................. 514/568, 714, 514/859, 861, 863, 864

[56] References Cited

U.S. PATENT DOCUMENTS

| | | | |
|---|---|---|---|
| 4,056,611 | 11/1977 | Young | 424/62 |
| 4,189,501 | 2/1980 | Fulton, Jr. | 514/859 |
| 4,694,021 | 9/1987 | Schweiger | 514/544 |
| 5,010,071 | 4/1991 | Bittler et al. | 514/178 |
| 5,047,249 | 9/1991 | Rothman et al. | 514/859 |

*Primary Examiner*—Shelley A. Dodson
*Attorney, Agent, or Firm*—Foley & Lardner

[57] ABSTRACT

Topical application to regions of tissue scarring of a composition comprising several ingredients commonly used in cosmetic products, such as benzoyl peroxide, leads to a reduction and a softening of scar tissue.

19 Claims, No Drawings

METHOD FOR TOPICAL TREATMENT OF SCAR TISSUE AND RELATED TISSUE REACTION TO TRAUMA

This application is a continuation of application Ser. No. 08/394,000, filed Feb. 24, 1995.

BACKGROUND OF THE INVENTION

The present invention relates to a method for softening and reducing cutaneous and subcutaneous scar tissue. More specifically, the present invention relates to a method for treating scar tissue by the topical application of a specific composition directly to areas of the body where scarring has occurred, for example, as a result of trauma accompanying surgery.

Advances in plastic surgery have ameliorated the problem of scarring that occurs, both in the layers of the skin (cutaneously) and in the region beneath the skin (subcutaneously) due to trauma associated with injury or surgical intervention. Nevertheless, there was heretofore little that could be done to normalize the appearance of specific scar tissue after sufficient time had passed for significant natural reduction of scar mass to have stopped.

It has been discovered in Schweiger, U.S. Pat. 4,694,021 ("the '021 patent"), that a composition possessing a consistency permitting it to be caked onto the region where scarring had occurred, advantageously led to a softening and reduction of scar tissue. In the '021 patent the preferable composition contained enough water, inter alia, to achieve the desired "caking" consistency, i.e., until the caked on composition dried and hardened. In fact, the preferred commercially available product of the '021 patent was MUDD®, hence, the composition preferably had the texture of a face pack or mask. This method for treating scar tissue by the topical application of this specific compound, therefore proved to be somewhat unpractical and unpopular in view of the inconvenience of applying the therapeutic preparation in the form of a bulky face mask. A need, therefore, exists to develop a method of treating scar tissue that is (1) easy and convenient to use, and (2) elicits superiorly effective results.

SUMMARY OF THE INVENTION

It is therefore an object of the present invention to provide a therapeutic method for treating scar tissue that is effective in normalizing the appearance of such tissue, even after the process of natural reduction of scar mass has ceased.

It is also an object of the present invention to provide a simple, noninvasive and relatively inexpensive method for softening and reducing both cutaneous and subcutaneous scar tissue.

It is a further object of the present invention to provide a compound with a practical and comfortable consistency for use in a method for softening and reducing both cutaneous and subcutaneous scar tissue.

In accomplishing the foregoing objects, there has been provided, in accordance with one aspect of the present invention, a method for treating scar tissue comprising the step of topically applying, to a body region where cutaneous or subcutaneous scarring has occurred, a therapeutically effective amount of a composition comprising benzoyl peroxide, an argillaceous absorbent and at least one ester of p-hydroxybenzoic acid. In a preferred embodiment, the aforesaid composition is applied, to the body region where scarring has occurred, in a sufficient amount such that a light to moderate layer of the composition covers substantially all of the scar-affected body region.

Additionally, in a preferred embodiment, the aforesaid composition is applied, to the body region where scarring has occurred by repeatedly applying light to moderate applications of a composition having an active ingredient of benzoyl peroxide lotion (hereinafter sometimes referred to as "the preferred composition"). The preferred composition is applied in this manner, allowing a half minute to a minute for the medication to settle in before gently applying the next portion of the composition over the prior layer. Each such application of the preferred composition slightly overlaps the underlying scar affected body region to maximize the effectiveness. With respect to subcutaneous scarring in the tip of the nose, the preferred composition is also similarly applied in a series of layers on the mucous membrane on the upper portion of each nostril flap.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

It has been discovered that a substance having a known use in cosmetic products, but no well-defined therapeutic effect in treating scar masses, can be employed via topical application to effect a reduction and a softening of scar tissue, even years after the trauma which caused the scarring. Although the physiological basis for this therapeutic effect is unclear, it is believed that topical application of the above-described substance induces (or enhances) natural mechanisms for the decalcifying or breaking up of fibrous material in scar-tissue masses. Such activity would be consistent with the observation, described in greater detail below, that topical applications of a composition in accordance with the present invention lead to a reduction of cutaneous and subcutaneous scar tissue and calcified bone overgrowth following rhinoplastic surgery.

A composition useful in treating scar tissue according to the present invention preferably comprises an argillaceous material, such as an aluminum silicate solid, which can act both as an absorbent and a base for the composition. Specifically, an aluminum silicate preferably used as an absorbent and a base for the composition is magnesium aluminum silicate The above-described composition further comprises benzoyl peroxide. Benzoyl peroxide has been used as a bleaching agent for flours, fats, oils and waxes, as well as a drying agent for unsaturated oils. According to Hawley, The Condensed Chemical Dictionary 120 (Van Nostrand Co. 1981), benzoyl peroxide has application as "a drying agent for unsaturated oils for pharmaceutical and cosmetic purposes." No role in affecting scar tissue, however, is known to have been ascribed to topical applications of benzoyl peroxide.

A third constituent of a composition employed in the present invention is a p-hydroxybenzoic acid ester, such as methyl or p-hydroxybenzoate ("methy paraben") and propyl p-hydroxybenzoate ("propylparaben"). Such esters are widely used in cold creams, eyeliners and liquid makeup products as preservatives and antimicrobial agents, but no therapeutic activity is known to be attributed to them. In the present invention, it is preferred that both methyl and propyl p-hydroxybenzoate are present in the topically applied composition.

A composition used pursuant to the present invention should also contain typical ingredients found in skin cleansers, such as emulsifiers, surfactants, stabilizers, solvents, etc., including, but not limited to, glyceryl monosterate, isopropyl palmitate, polyethylene glycol-(PEG)-20 stearate, propylene glycol, stearic acid, water, xanthan gum and zinc stearate.

In any event, it is preferred that the primary, benzoyl peroxide-containing composition be applied substantially to the entire region of the scar tissue, preferably in an amount sufficient to form an effective layer. "Substantially" in this context denotes that the therapy of the present invention does not require, for effectiveness, a total coverage of the scarred region. Nevertheless, it is preferred that the body area affected by scarring be completely covered, with a slight overlapping and tapering of the layer into surrounding regions not so affected.

It is also preferable that the composition used for softening and reducing cutaneous and subcutaneous scar tissue possess a consistency which is light to moderate in weight and texture, therefore providing an effective yet comfortable vehicle for topically delivering a pharmaceutically effective amount of the preferred composition.

To this end, a composition that is particularly preferred for use in treating scar tissue according to the present invention includes %10 Benzoyl Peroxide Lotion (manufactured for KMart Corporation, Troy Mich.), an acne medication having a formulation comprising %10 benzoyl peroxide, glyceryl monosterate, isopropyl palmitate, magnesium aluminum silicate, methylparaben, propylparaben, PEG-20 stearate, propylene glycol, stearic acid, water, xanthan gum, and zinc stearate, which comes within the preceding description.

Periodic topical applications of %10 Benxoyl Perioxide Lotion, to a region of the nose which had been scarred, both cutaneously and subcutaneously, by major rhinoplastic surgery or otherwise were associated with a reduction in the mass of scar tissue, a concomitant softening of remaining scar tissue, and a recession in calcium overgrowth which had caused an apparent thickening of the nasal bone.

The present invention was made when a 10% Benzoyl Perioxide Lotion, marketed to help heal acne, was applied for the purpose of alleviating a bacterial infection in the right nasal flap. Scar tissue from a surgical rhinoplasty procedure many years earlier was located in the nasal tip at the time of this treatment for the bacterial infection. After four days of treatment of the infection with 10% Benzoyl Peroxide Lotion, not only had the discomfort of the infection been alleviated, as expected, but scar tissue reduction and a more normal appearance of the nasal tip also occurred, the result of which was quite unexpected. Continued application of 10% Benxoyl Peroxide Lotion resulted in continued scar tissue reduction in the ensuing months. Additionally, the scar tissue softened as it was being reduced in size. These effects of the therapy, following the present invention, were particularly unexpected since the surgery which caused the scarring that was treated had taken place approximately seventeen to eighteen years earlier, i.e., the treatment was effective well after significant postoperative normalization of the damaged tissue had ceased.

Maximum benefit of the present invention is realized approximately one to one and a quarter hours from the time each treatment of the 10% Benzoyl Peroxide Lotion is applied. It is believed that maximum benefit occurs while the lotion is moist, therefore corresponding to the aforementioned time frame for application of the preferred composition. Layering of the composition helps assure that the lotion will not dry too quickly and thus shorten the benefit period. After the treatment, the dried residue is washed off with water. A light application of non-prescription hydrocortisone cream and/or moisturizer may be used to help prevent or ameliorate redness and flaking.

A multiplier type effect may be shown when two to three topical treatments of the %10 Benzoyl Peroxide Lotion are effected in close proximity of each other, generally from one to fifteen minutes apart. The results of such an effect may offer heightened and/or accelerated scar tissue reduction over the results elicited from the same number of treatments spaced a day apart.

Another enhancement technique, which may lengthen and/or strengthen the therapeutic effect of the preferred composition according to the present invention, is to add a moderate to heavy application of the %10 Benxoyl Peroxide Lotion twenty-five to thirty-five minutes after application of the original layers and while the first application is still moist.

In any event, if two or more treatments are made several minutes apart in order to help achieve accelerated, heightened, lengthened or strengthened results, it is preferable that the applications of the preferred composition, particularly the latter ones, be preceded with a light application of non-prescription hydrocortisone cream and/or a light application of moisturizing lotion. Additionally, the last layered treatment should preferably be followed by application of the hydrocortisone cream and possibly a moisturizing lotion (as opposed to a moisturizing cream, because in one example the cream tended to promote bacterial inflammation), in order to avoid irritation to the area being treated.

In light of the instant invention, it is believed that benzoyl peroxide is an agent which generally helps the body repair itself from excess tissue formations and fluids caused by tissue damage. Such damage could occur from outside trauma, i.e., burned tissue, or also from naturally occurring events such as arthritis. Accordingly, it is asserted that large quantities of 10% Benxoyl Peroxide Lotion could reduce healing time and degree of "permanency" from injury and may help decalcify and reduce arthritic malformations in the hand. Additionally, it is purported that an appropriately palatable solution of benzoyl peroxide could be injected into a joint's synovial tissue in order to help alleviate arthritic problems. In this vein, a palatable solution of benzoyl peroxide could be effective in related surgical uses.

However, according to dermatological consultation, about 2% of the population is allergic to 10% benzoyl peroxide. It is conceivable, therefore, that a person with the need to use such a composition for softening and reducing cutaneous and subcutaneous scar tissue, could develop an allergic reaction immediate to or following continued application of such a composition. The consequences could result in a simple or swelling rash (the norm) and/or mild asthma (dermatological consultation indicates this type of reaction is unusual). Additionally, in this regard, the literature on the 10% Benxoyl Peroxide Lotion, marketed by KMart Corporation, states under "warnings":

For external use only. Using other topical acne medications at the same time or immediately following use of this product may increase dryness or irritation of the skin. If this occurs, only one medication should be used unless directed by a physician. Do not use this medication if you have very sensitive skin or if you are sensitive to benzoyl peroxide. This product may cause irritation, characterized by redness, burning, itching, peeling, or possibly swelling. Mild irritation may be reduced by using the product less frequently or in a lower concentration. If irritation becomes severe, discontinue use; if irritation still continues, consult a physician. Keep away from eyes, lips, and mouth. In case of accidental ingestion, seek professional assistance or contact a Poison Control Center immediately. Avoid contact with hair, fabrics or carpeting as benzoyl peroxide will cause bleaching.

It is possible, with those persons with traditionally sensitive skin, that the application of the 10% Benxoyl Peroxide Lotion be routinely preceded with an application of non-prescription 1% hydrocortisone cream and post-treated with the same cream to ameliorate redness and dryness. With or without the 1% hydrocortisone cream, scar tissue softening and reduction occurred.

The forgoing invention has been described with reference to particularly preferred embodiments. Those skilled in the art recognize that various modifications can be made to the invention without departing from the spirit and scope thereof.

What is claimed is:

1. A method for decalcifying bone mass or reducing fibrous material in scar tissue masses comprising the step of topically applying, to a body region where cutaneous or subcutaneous scarring or calcified bone overgrowth has occurred, in combination, (a) a therapeutically effective amount of a composition comprising as an active ingredient benzoyl peroxide, and (b) an argillaceous absorbent and at least one ester of p-hydroxybenzoic acid.

2. A method according to claim 1, wherein said absorbent consists essentially of an aluminum silicate.

3. A method according to claim 2, wherein said aluminum silicate absorbent consists essentially of magnesium aluminum silicate.

4. A method according to claim 1, wherein said ester of p-hydroxybenzoic acid is at least one ester selected from the group consisting of methyl p-hydroxybenzoate and propyl p-hydroxybenzoate.

5. A method according to claim 1, wherein said composition further comprises one or more skin cleanser adjutants selected from a group consisting of emulsifiers, surfactants, stabilizers and solvents.

6. A method according to claim 1, wherein said amount of said composition applied to said body region is sufficient to form a layer of said composition which covers substantially all of said region.

7. A method according to claim 6, wherein a layer of said therapeutically effective amount of a composition is applied in a light to moderate thickness.

8. A method according to claim 7, further comprising, prior to said topical application of said layer of said composition, the step of applying to said body region an amount of a second composition which is sufficient to form a layer of said second composition covering substantially all of said region, said second composition consisting essentially of a hypoallergenic cream.

9. A method according to claim 7, further comprising, following said topical application of said layer of said composition, the step of applying to said body region an amount of a second composition which is sufficient to form a layer of said second composition covering substantially all of said region, said second composition consisting essentially of said hypoallergenic cream.

10. A method according to claim 8, wherein said second composition consists essentially of %1 hydrocortisone cream and/or a moisturizing lotion.

11. A method according to claim 9, wherein said second composition consists essentially of %1 hydrocortisone cream and/or a moisturizing lotion.

12. A method according to claim 1, wherein natural reduction of scar mass in said body region has ceased prior to application of said composition.

13. A method according to claim 1, wherein said composition comprises benzoyl peroxide, an argillaceous absorbent, at least one ester of p-hydroxybenzoic acid and one or more skin cleanser adjutants selected from a group consisting of emulsifiers, surfactants, stabilizers and solvents.

14. The method as claimed in claim 1, wherein the method decalcifies bone mass.

15. A method for decalcifying bone mass comprising the step of topically applying, to a body region where cutaneous or subcutaneous scarring or calcified bone overgrowth has occurred, in combination, (a) a therapeutically effective amount of a composition comprising as an active ingredient benzoyl peroxide, and (b) an argillaceous absorbent and at least one ester of p-hydroxybenzoic acid.

16. The method according to claim 15, wherein said absorbent consists essentially of magnesium aluminum silicate.

17. The method according to claim 15, wherein said ester of p-hydroxybenzoic acid is at least one ester selected from the group consisting of methyl p-hydroxybenzoate and propyl p-hydroxybenzoate.

18. The method according to claim 15, wherein said composition further comprises one or more skin cleanser adjutants selected from a group consisting of emulsifiers, surfactants, stabilizers and solvents.

19. The method according to claim 15, wherein said composition comprises benzoyl peroxide, an argillaceous absorbent, at least one ester of p-hydroxybenzoic acid and one or more skin cleanser adjutants selected from a group consisting of emulsifiers, surfactants, stabilizers and solvents.

* * * * *